United States Patent
Kresch et al.

[11] Patent Number: 5,785,640
[45] Date of Patent: Jul. 28, 1998

[54] METHOD FOR TREATING FEMALE INCONTINENCE

[76] Inventors: Arnold J. Kresch, 780 Welch Rd., Suite 206, Palo Alto, Calif. 94304; Tim J. Kovac, 33 Ashler Ave., Los Gatos, Calif. 95030

[21] Appl. No.: 652,887

[22] Filed: May 23, 1996

[51] Int. Cl.$^6$ ............................................ A61F 2/00
[52] U.S. Cl. .................................. 600/29; 600/30
[58] Field of Search .................... 600/29–31; 128/834, 128/DIG. 25

[56] References Cited

U.S. PATENT DOCUMENTS

| | | | |
|---|---|---|---|
| 2,422,377 | 6/1947 | Waterbury | 128/834 |
| 3,372,695 | 3/1968 | Beliveau et al. | |
| 4,019,498 | 4/1977 | Hawtrey et al. | 128/1 |
| 4,139,006 | 2/1979 | Corey | 128/127 |
| 4,669,478 | 6/1987 | Robertson | 128/630 |
| 4,920,986 | 5/1990 | Biswas | 128/885 |
| 4,955,858 | 9/1990 | Drews | 604/8 |
| 5,007,894 | 4/1991 | Enhorning | 600/29 |
| 5,036,867 | 8/1991 | Biswas | 128/885 |
| 5,090,424 | 2/1992 | Simon et al. | 128/885 |
| 5,256,133 | 10/1993 | Spitz | 600/29 |
| 5,336,208 | 8/1994 | Rosenbluth et al. | 604/329 |
| 5,352,182 | 10/1994 | Kalb et al. | 600/30 |
| 5,417,226 | 5/1995 | Juma | 128/885 |
| 5,479,945 | 1/1996 | Simon | 128/885 |
| 5,483,976 | 1/1996 | McLaughlin et al. | 128/885 |

*Primary Examiner*—John P. Lacyk
*Assistant Examiner*—Rosiland Kearney
*Attorney, Agent, or Firm*—Townsend and Townsend and Crew LLP

[57] ABSTRACT

A female urinary incontinence device (2) and method comprises an elongate body (4) and a pair of anterior support members (6, 8) extending from the proximal end of the elongate body. The anterior support members are spaced from each other and configured for elevating and/or supporting the superior vaginal tissue (122) on each side of the bladder neck (106) to normalize urodynamic parameters without completely occluding the urethra (108) so that the patient may urinate or not urinate, if desired. A pair of posterior support members (10, 12) extend from the distal end of the elongate body for engaging the posterior vaginal wall (120) to provide longitudinal support to the anterior support members. The device may be folded axially between a collapsed position for insertion into the vagina (100) and an expanded position for supporting the bladder neck to offer counterpressure to intra-bladder pressure so that continence is preserved.

9 Claims, 7 Drawing Sheets

METHOD FOR TREATING FEMALE INCONTINENCE

BACKGROUND OF THE INVENTION

1. Field of the Invention

The present invention relates generally to incontinence and more particularly to a non-surgical device and method for controlling female urinary incontinence.

Urinary incontinence in women has long been a serious problem that requires medical attention. Stress incontinence, the involuntary loss of urine during exertional activities, is the typical cause of incontinence and is most prevalent among women aged 35-65 and those who have had multiple vaginal deliveries. This condition may be caused either by a weakness of the intrinsic urethral sphincter muscle or by the abnormal descent of the urethra and bladder neck below the pelvic floor muscle with increased intra-abdominal pressure. During coughing, sneezing, laughing, physical exercise or the like (i.e., when strain is placed upon the bladder), the patient involuntarily releases a small volume of urine from the urethra. This involuntary urine release is unpleasant, embarrassing and may contaminate the genital sections of the woman.

The descent of the bladder neck that contributes to female incontinence may often be repaired with surgical procedures. Surgical repair of female incontinence generally involves securing the paraurethral tissues to the periosteum of the pubic bone or the rectus facia to elevate the bladder neck above the pelvic floor muscle and thereby distribute pressure equally to the bladder, bladder neck and pelvic urethra. This operation may be performed through an incision in the vaginal wall or the abdomen. While this surgery has often proved successful, it can be traumatic to the patient and, in elderly or infirm patients, the risk of surgery may be too great to justify the surgical procedure. In addition, while the surgical techniques are often effective for periods of several years, the urethra may break loose following extensive activity, thereby causing a reoccurrence of the urinary incontinence condition.

The problems associated with surgical procedures have resulted in the development of a number of non-surgical incontinence devices. These devices are generally inserted into the vagina or directly into the urethra by the surgeon or the patient. Incontinence devices inserted into the urethra typically include an occluding member for blocking flow of urine through the bladder neck during sudden tensioning of the abdominal muscles. Incontinence devices inserted into the vagina are typically expanded, e.g., by inflating an expandable member such as a balloon, in an upward direction against the anterior wall of the vagina to apply pressure against the bladder neck. This pressure inhibits or completely prevents the flow of urine through the urethra.

Existing non-surgical urinary incontinence devices suffer from a number of drawbacks. For example, many of these devices tend to block all or substantially all flow of urine from the bladder. Therefore, when a patient needs to urinate, the device must be removed from the vagina or urethra or the device must be collapsed to remove the pressure applied against the bladder neck (e.g., by deflating a balloon). In an attempt to solve or at least mitigate this problem, incontinence devices have been developed that support the upper urethra without completely blocking the bladder neck so that the patient may urinate with the device in place. These devices, however, are generally large and intrusive and, therefore, are uncomfortable to wear, and they may irritate the tender mucosal tissue within the vagina after a period of time (particularly when the patient is active, e.g., during physical exercise). In addition, these devices are relatively expensive to manufacture and, therefore, they are either designed for re-use and/or they must remain within the patient's vagina for a relatively long period of time (i.e., 24 hours or longer).

For these and other reasons, it would be desirable to provide methods and devices for controlling urinary incontinence in women. These methods and devices should be capable of elevating the bladder neck and/or supporting the vaginal tissue on each side of the urethra to offer counter-pressure to intra-abdominal pressure and thereby preserve continence. Furthermore, this female incontinence device should be minimally intrusive to maximize comfort and minimize irritation of the tender mucosal tissues within the vagina. Additionally, the female incontinence device should be relatively inexpensive to manufacture and easy to remove and insert so that it can used for shorter time periods, such as during physical activity, if desired.

2. Description of the Background Art

U.S. Pat. No. 4,920,986 to Biswas describes an intervaginal device for controlling urinary incontinence that includes a body member with a forward portion for engaging the anterior vaginal wall adjacent the bladder neck to lift the neck and base of the bladder above the pelvic floor muscle thereby maintaining continence. U.S. Pat. Nos. 5,386,836 and 5,007,894 describe female incontinence devices that incorporate inflatable body members that may be inserted into the vagina and inflated into a position for maintaining continence. The body members include two opposed projections that form a cradle for receiving and supporting the neck of the bladder. U.S. Pat. No. 5,417,226 to Juma describes an incontinence device that may be inserted directly into the urethra and incorporates a flexible disk for occluding the bladder neck during sudden tensioning of the abdominal muscles.

SUMMARY OF THE INVENTION

The present invention provides a non-surgical device and method for controlling female urinary incontinence. The device comprises an elongate body with proximal and distal ends and one or more anterior support members extending from the proximal end of the elongate body. When the device includes more than one anterior support member, they are movable between a collapsed or longitudinal position, where the device is configured for insertion into the patient's vagina, and an expanded position, where the anterior support members are spaced apart from each other for supporting and/or elevating the bladder neck to minimize incontinence. The elongate body and anterior support members have a relatively narrow, non-intrusive profile that generally conforms to the patient's vagina, thereby increasing comfort and minimizing irritation of the tender mucosal tissues within the vagina. In addition, the anterior support members are configured to normalize the patient's urodynamic parameters without completely occluding the urethra so that the patient may urinate, if desired.

In a specific configuration, the anterior support members are first and second arms extending laterally and longitudinally from the proximal end of the elongate body and first and second hemispherical bladder support members contiguous with the first and second arms, respectively. The hemispherical bladder support members have a curved, atraumatic surface for engaging the vaginal tissue around the bladder neck, thereby minimizing irritation of this tissue. The arms extend away from the elongate body so that, when the device is suitably positioned within the patient's vagina, the hemispherical support members elevate and support the bladder neck above the pelvic floor muscle. The anterior support members and the elongate body are preferably moved into the collapsed position by folding them together along the longitudinal axis of the body. In this manner, the device can be quickly and easily folded and then introduced into the vagina by the surgeon or the patient. The anterior support members are preferably biased towards the expanded position (e.g., by the elastic properties of the support members) so that they will automatically expand away from each other once the surgeon or patient releases them within the patient's vagina.

The incontinent device of the present invention further includes one or more posterior support members extending from the distal end of the elongate body for engaging the posterior vaginal wall. The posterior support member(s) brace the elongate body between the posterior vaginal wall and the urethra to provide longitudinal support to the anterior support members. In a specific configuration, a pair of posterior support members are spaced apart from each other in the expanded configuration such that they contact the posterior vaginal wall on either side of the colon and/or rectum. Preferably, the posterior support members are first and second arcuate paddles extending laterally and longitudinally from the distal portion of the elongate body to provide a laterally displaced load against the patient's pelvic structure. In this manner, the posterior support members provide sufficient longitudinal support to the anterior support members to keep these members in position against the bladder neck, while minimizing interference with the soft tissue at the colon and/or rectum.

In an exemplary embodiment, the device is manufactured from a disposable material, such as paper, paper fiber, cotton or a flexible, elastic and inexpensive material, such as plastic, elastomers, PET, polycarb, ABS, silicone rubber and the like, so that the patient can simply remove and dispose the device when desired. In this manner, a patient suffering from stress incontinence may insert the device for a specific, relatively short, time period, such as during physical activity, and then remove and dispose the device at the conclusion of that activity.

The incontinence device of the present invention may be inserted into the vagina manually or with an insertion device or introducer. In the latter configuration, the introducer preferably comprises a hollow shaft having an inner lumen sized to receive the incontinence device in the collapsed position. The shaft is inserted into the patient's vagina by the physician or the patient so that its distal end is suitably positioned adjacent the patient's bladder neck, and the incontinence device is propelled through the distal end of the hollow shaft with a pusher mechanism, such as a plunger or the like. The incontinence device expands upon release from the hollow shaft, and the anterior support members are engaged against the bladder neck. The physician or patient then removes the shaft, allowing the posterior support member(s) of the device to move into position against the posterior vaginal wall.

Other features and advantages to the invention will appear from the following description in which the preferred embodiment has been set forth in detail in conjunction with the accompanying drawings.

DESCRIPTION OF THE SPECIFIC EMBODIMENTS

Figure 1:
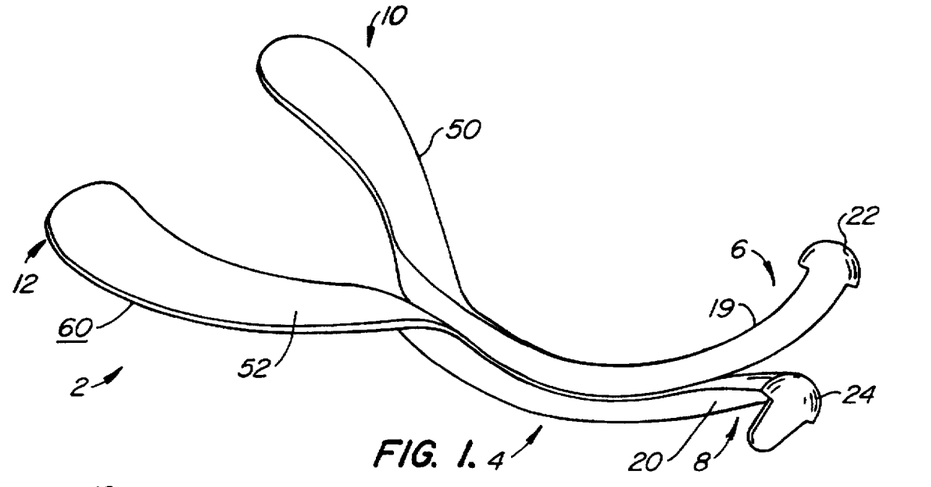
FIG. 1 is a perspective view of a female urinary incontinence device according to the present invention.

Referring to the drawings in detail, wherein like numerals indicate like elements, a female urinary incontinence device 2 is illustrated according to the principles of the present invention. As shown in FIG. 1, incontinence device 2 generally comprises an elongate body 4 and first and second anterior support members 6, 8 for supporting and/or elevating the patient's bladder neck. Device 2 further includes first and second posterior support members 10, 12 for bracing the body 4 between the posterior vaginal wall and the urethra to provide longitudinal support to the anterior support members.

Figure 2:
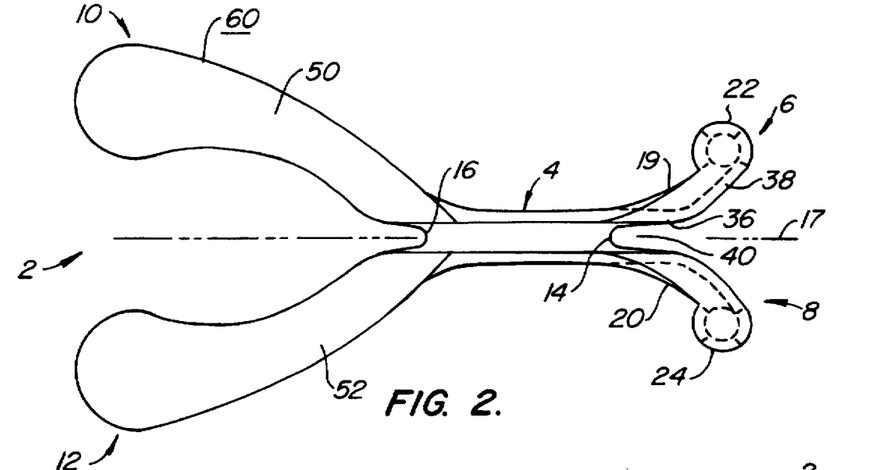
FIG. 2 is a top view of the incontinence device of FIG. 1.
Figure 3:
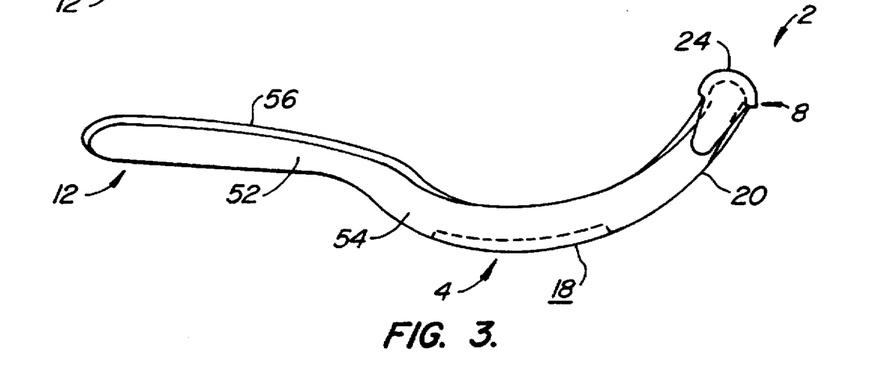
FIG. 3 is a side view of the incontinence device of FIG. 1.
Figure 4A:
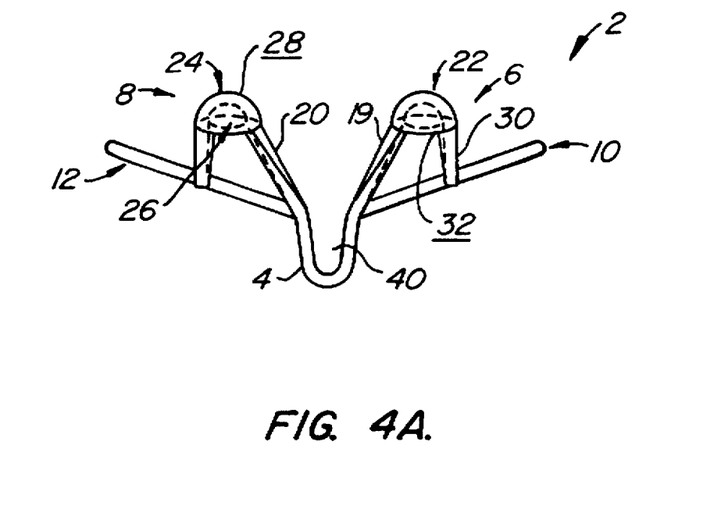
FIGS. 4A and 4B are front views of the incontinence device of FIG. 1.

Referring to FIGS. 1–4, elongate body 4 has a proximal end 14, a distal end 16 and a longitudinal axis 17 therebetween. As best shown in FIGS. 4A and 4B, body 4 preferably has a generally U-shaped transverse cross-section to facilitate folding body 4 lengthwise along the longitudinal axis 17 into a collapsed, longitudinal position for insertion into the patient's vagina 100 (see FIGS. 5 and 7). Of course, it will be recognized that body 4 may have cross-sectional shapes other than U-shaped, such as solid, tubular and the like. The dimensions of elongate body 4 (i.e., length, width and shape) generally conform to the dimensions of the vagina 100 so that incontinence device 2 is minimally intrusive to the patient. To that end, body 4 will usually have a width in the range of 0.05 to 0.7 inch and preferably in the range of 0.2 to 0.4 inch and a length in the range of 0.5 to 1.0 inch. In addition, body 4 defines an arcuate lower surface 18 for bearing against the posterior vaginal wall 120, as shown in FIGS. 3 and 5. Lower surface 18 has a curvature substantially similar to the curvature of the posterior vaginal wall 120 so that elongate body 4 generally conforms to a portion of this wall. Alternatively, lower surface 18 may be substantially straight and body 4 constructed of a flexible material that will deform into a curvature that conforms to the posterior vaginal wall 120.

Figure 5:
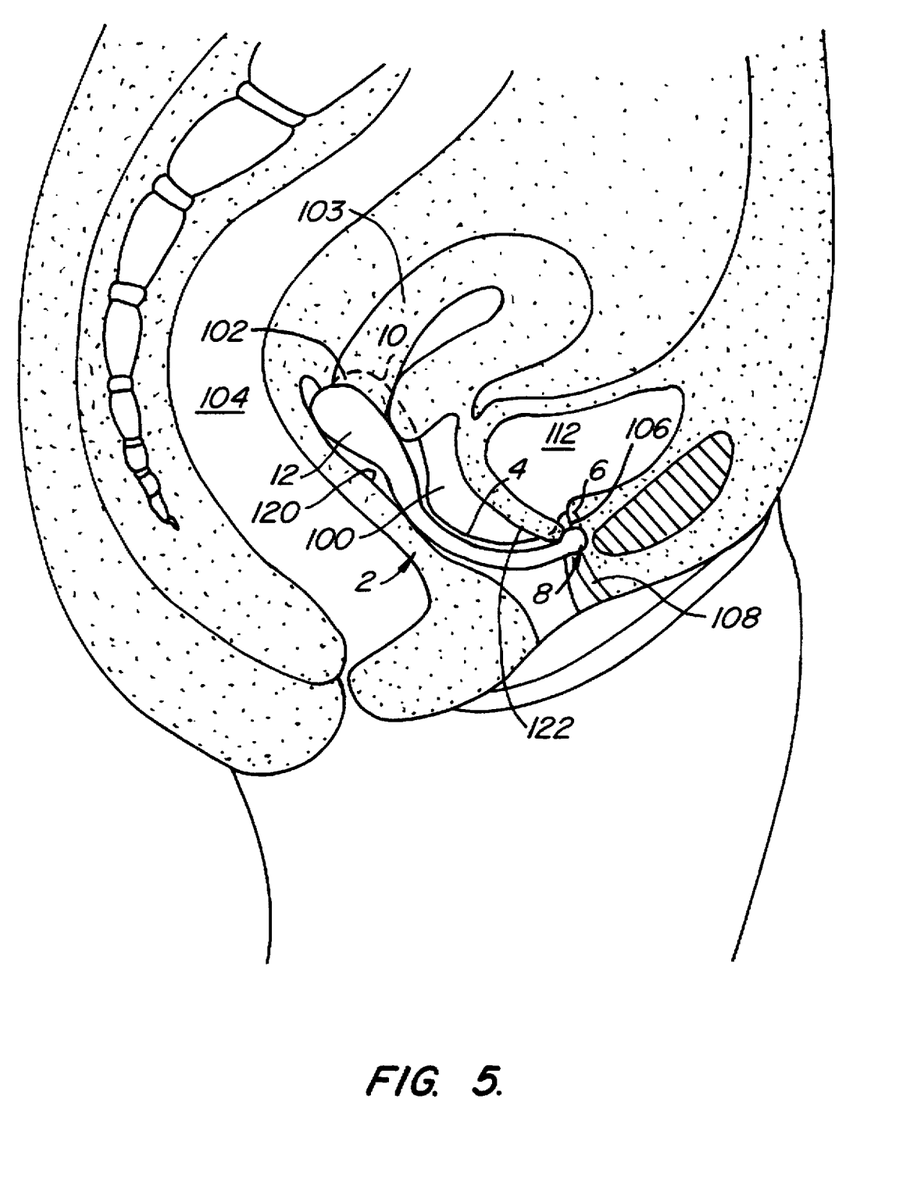
FIG. 5 is a transverse cross-sectional view of the female pelvic organs illustrating the female incontinence device of the present invention in place within the vagina.
Figure 6:
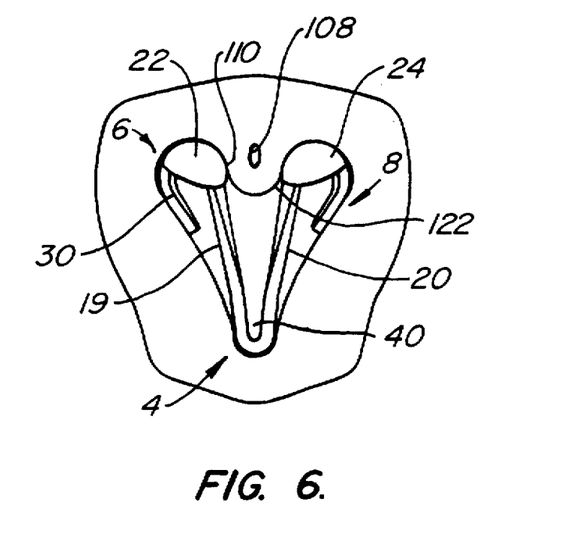
FIG. 6 is a top cross-sectional view of the female incontinence device of FIG. 1 within the patient's vagina, illustrating anterior support members of the incontinence device elevating and supporting the bladder neck.

Anterior support members 6, 8 each comprise an arm 19, 20 contiguous with and extending from proximal end 14 of body 4 and a bladder support member 22, 24 attached to arms 19, 20, respectively. As best shown in FIG. 4A, bladder support members 22, 24 are preferably hemispherical and define an inner cavity 26 and a curved, atraumatic surface 28 for pressing upward against the tissue immediately lateral to the urethra 110 (FIGS. 5 and 6). Bladder support members 22, 24 preferably comprise an elastic, atraumatic material, such as paper, cotton, polymers and the like, for engaging the soft anterior vaginal tissue 122 around the bladder neck. Bladder support members 22, 24 preferably have radius of curvature of about 0.1 to 0.3 and a width of about 0.2 to 0.3 inch. It should be understood that bladder support members 22, 24 may comprise a variety of other shapes and sizes so long as the support members provide the necessary support to the muscles surrounding the bladder neck 106 in a generally atraumatic manner that will minimize irritation and/or damage to the vaginal tissue.

Figure 4B:
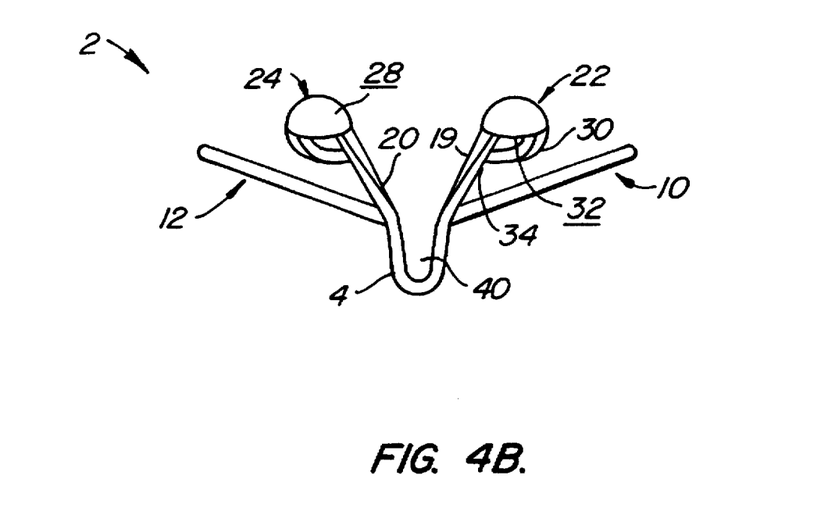

As shown in FIGS. 4A and 4B, bladder support members 22, 24 each include a tab 30 extending downward from a lower surface 32 of members 22, 24. Tabs 30 serve to protect the tender vaginal tissue from the edges between the lower and curved surfaces 32, 28 of bladder support members 22, 24. To facilitate the manufacture of tabs 30, each tab is configured for movement between a first, as manufactured, position (FIG. 4A), where tabs 30 extend substantially vertically downward from lower surface 32 of members 22, 24, and a second use position (FIG. 4B), where tabs 30 are folded upward so that the tip 34 of each tab 30 extends substantially parallel to the lower surface 32 of support members 22, 24. In this manner, tabs 30 may be manufactured, e.g., injection molded or thermoformed, in the vertical first position and then folded into the second, use position prior to insertion of device 2 into the vagina 100. Of course, it will be recognized by those in the art that a variety of other means may be used to smooth the edges of support members 22, 24, including folding a hemispherical tab (not shown) underneath the lower surface 32 of support members 22, 24.

Referring to FIGS. 1, 2, 5 and 6, arms 19, 20 each extend laterally and longitudinally from proximal end 14 of elongate body 4 to space bladder support members 22, 24 on either side of the bladder neck 106). In addition, arms 19, 20 extend transversely to the plane of elongate body 4 such that, when lower surface 18 bears against the posterior vaginal wall 120, bladder support members 22, 24 are suitably positioned to elevate and support the bladder neck 106 above the pelvic floor muscle (not illustrated). Preferably, arms 19, 20 each include a first portion 36 extending from proximal end 14 substantially parallel to body 4 and a second portion 38 contiguous with first portion 36 and extending laterally outward from body 4. First and second arm portions 36, 38 are slender, non-intrusive and relatively easy to manipulate so that the surgeon or patient can quickly and easily position bladder support members 22, 24 against the bladder neck 106. First portions 36 of arms 19, 20 define a cradle 40 therebetween for receiving and supporting the neck of the patient's bladder (see FIG. 6). First portions 36 will usually be spaced a distance of 0.2 to 0.5 inch and preferably 0.25 to 0.3 inch from each other. These dimensions, of course, will vary depending on the requirements of the individual patient.

Second portions 38 of arms 19, 20 extend laterally outward to space bladder support members 22, 24 a suitable distance apart for positioning on either side of the bladder neck. Bladder support members 22, 24 will usually be spaced apart a distance of 0.5 to 1.0 inch and preferably 0.6 to 0.8 inch. Bladder support members 22, 24 provide tension to the muscle on either side of the urethra 108, thereby allowing the muscle to counter bladder pressure and/or intra-abdominal pressure to preserve continence. Note that the anterior support member 6, 8 are preferably designed so that the bladder neck or urethra is partially occluded or occluded by tissue tension adequate to prevent involuntary and/or voluntary urination, but not completely blocked off so that the patient may urinate, if desired.

Referring to FIG. 1, posterior support members 10, 12 preferably comprise arcuate paddles 50, 52 contiguous with and extending laterally and longitudinally from distal end 16 of elongate body 4. As best shown in FIG. 2, paddles 50, 52 include a first portion 54 that extends transversely to the plane of elongate body 4 and a second portion 56 that extends substantially parallel to the plane of body 4. Second portions 56 of paddles 50, 52 each define outer load distributing surfaces 60 (FIGS. 1 and 2) for bearing against the posterior vaginal wall 121 and the patient's pelvic structure, as discussed in detail below. Paddles 50, 52 each have an arcuate shape designed to act in a cupping manner when displaced perpendicularly to the plane formed by the paddles 50, 52. This cupping action allows paddles 50, 52 to bear laterally against the patient's pelvic structure.

Referring to FIGS. 3 and 5, second portions 56 of paddles 50, 52 are spaced apart a distance sufficient to engage and bear against the posterior vaginal wall on either side of the patient's colon 104 and/or rectum (not shown). This configuration minimizes contact between the paddles 50, 52 and the patient's colon 104 or rectum so to minimize loading and possibly herniating the soft tissue of the colon 104. In addition, the spaced configuration of paddles 50, 52 effectively avoids any possible obstruction of the patient's bowel movements. For a typical patient, second portions 56 will be spaced a distance in the range of 0.5 to 2.0 inches and preferably 1.0 to 1.5 inches.

Referring to FIG. 5, incontinence device 2 is sized and configured to effectively elevate, support and/or occlude the bladder neck 106 of the patient. To this end, posterior support members 10, 12 are sized to brace elongate body 4 and anterior support members 6, 8 between the posterior vaginal wall 121 and the urethra 108 to provide longitudinal support to anterior support members 6, 8, thereby offering counterpressure to intra-abdominal pressure so that continence is preserved. Usually, device 2 will have an overall length of about 3.0 to 5.0 inches and preferably 3.5 to 4.0 inches. In addition, body 4 will preferably have a smaller length than posterior and anterior support members 6, 8, 10, 12. Specifically, posterior support members will usually have a length in the range of 1.0 to 3.0 inches and more preferably 1.5 to 2.5 inches and anterior support members (including arms 19, 20 and bladder support members 22, 24) will have a length in the range of 0.8 to 1.5 inches. The relative dimensions of the support members and body of device 2 allow anterior support members 6, 8 to form cradle 40 for receiving and supporting the bladder neck 106 and facilitate manipulation and placement of anterior support members 6, 8 against the bladder neck 106 (FIG. 6). In addition, posterior support members 8, 10 are substantially longer than body 4 so that a relatively long inner space is formed between the posterior support members 10, 12. This space effectively ensures that the support members will not interfere with the patient's colon 104.

Incontinence device 2 is movable between a collapsed or longitudinal position (FIG. 7), where the device is configured for insertion into the patient's vagina 100, and an expanded position (FIG. 5), where the device is configured to form a brace between the posterior vaginal wall 120 and the urethra 108 to minimize incontinence. In a preferred configuration, elongate body 4 is configured to fold axially about the longitudinal axis such that posterior and anterior support members 6, 8, 10, 12 move towards each other into a substantially longitudinal configuration (see FIG. 7). Preferably, incontinence device 2 will have a maximum lateral dimension of 0.3 to 1.0 inches in the longitudinal or collapsed position.

Incontinence device 2 comprises a flexible, biocompatible material, such as plastic, paper, cotton, polymers or the like, that may be folded into the longitudinal configuration and that has a sufficient degree of elasticity to automatically unfold into the expanded position after being inserted into the patient's vagina. In a preferred configuration, device 2 will be constructed of a material that is relatively inexpensive and easy to manufacture. In this manner, incontinence device 2 is disposable so that the patient can insert the device for a relatively short period of time, if desired (e.g., in preparation for physical exercise and the like). The disposable material may comprise a variety of relatively inexpensive material such as cardboard, paper, plastic and the like.

In a specific configuration, incontinence device 2 will comprise a material that degrades after a period of time within the vagina or when the patient actuates a trigger mechanism, e.g., pulling on a string 128 (FIGS. 8A and 8B) attached to device 2. In this manner, the incontinence device may be automatically disposed when, for example, the patient urinates. For this configuration, device will be constructed of a material that gradually loses its integrity, such as fiber binders that degrade in a moist environment.

Figure 7:
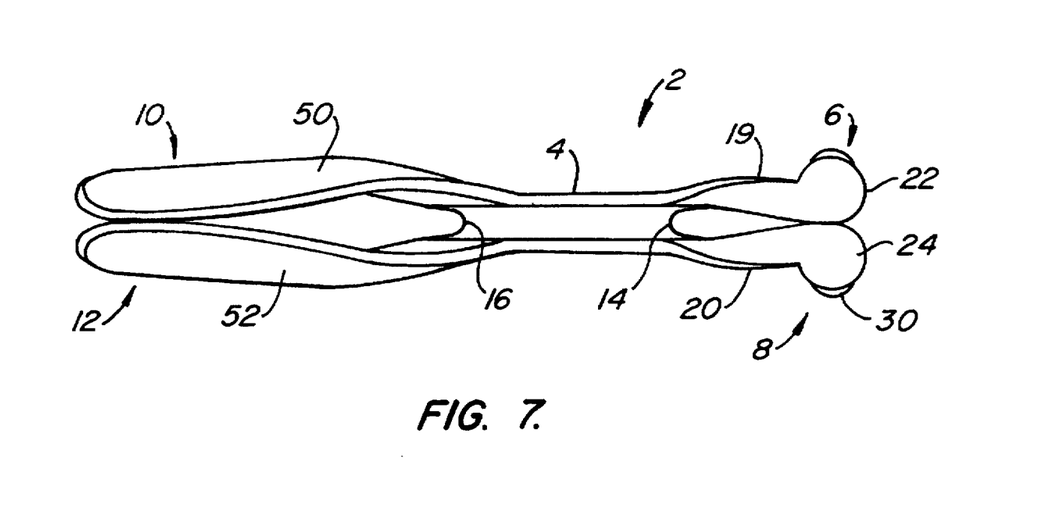
FIG. 7 is top view of the incontinence device of FIG. 1 in a collapsed, longitudinal position for insertion into the vagina.

Referring to FIGS. 5-7, the method of the present invention for inserting and removing female incontinence device 2 will now be described. As shown in FIG. 7, device 2 is folded into the longitudinal configuration such that anterior and posterior support members 6, 8, 10, 12 are in contact or in close proximity with each other. Device 2 is then introduced into the vagina 100 until posterior support members 10, 12 reach the posterior fornix 102 of the uterus 103 (FIG. 5). The device may be inserted into the vagina 100 in the doctor's office or by the patient at home. The insertion is similar to that of a diaphragm or tampon. As device 2 approaches the proper location, device 2 is allowed to unfold within the vagina 100 so that posterior support members 10, 12 bear laterally outward against the pelvic structure on either side of the colon 104. The doctor or patient then locates anterior support members 6, 8 to ensure that they are on each side of the upper urethra 108 and that members 19, 20 press up against the bladder neck 106.

As shown in FIG. 6, anterior support members 6, 8 exert supporting pressure against the anterior vaginal wall 110, laterally and adjacent to each side of the urethra to allow tissue between the vaginal mucosa and the urethra 108 produce a lateral pressure upon the upper section of the urethra 108 or the bladder neck 106. This pressure provides a slight reduction in the cross-sectional area of the urethra 108 and provides the muscles of the bladder neck 106 with tension to resist pressure. In this manner, the muscles will offer counterpressure when inter-abdominal and/or intra-bladder 112 pressure is suddenly raised as it is during coughing, sneezing, laughing and physical exercise. The inter-abdominal pressure is transmitted to the upper urethra so that the closure pressure remains positive regardless of the changes in the intra-abdominal pressure such that continence is preserved. Posterior support members 10, 12 bear laterally against the pelvic structure to brace anterior support members 6, 8 against the bladder neck 106, thereby effectively ensuring that the device remains in place as shown in FIG. 5.

After device 2 is inserted within the vagina 100, the patient may proceed with normal physical activities charac-teristic of everyday life. Since the device supplements the natural uretal muscle action of the patient, it is generally not necessary to remove device 2 when the patient desires to urinate. On the other hand, since the device is disposable and relatively inexpensive, the patient may remove device 2 after the physical activity has been completed. To accomplish this, the patient grasps one or both of the anterior support members 6, 8 or a proximal portion of body 4 and folds device 2 completely or partially along the longitudinal axis to decrease its profile. Device 2 is then removed from the vagina, where it can be suitably disposed.

Figure 8A:
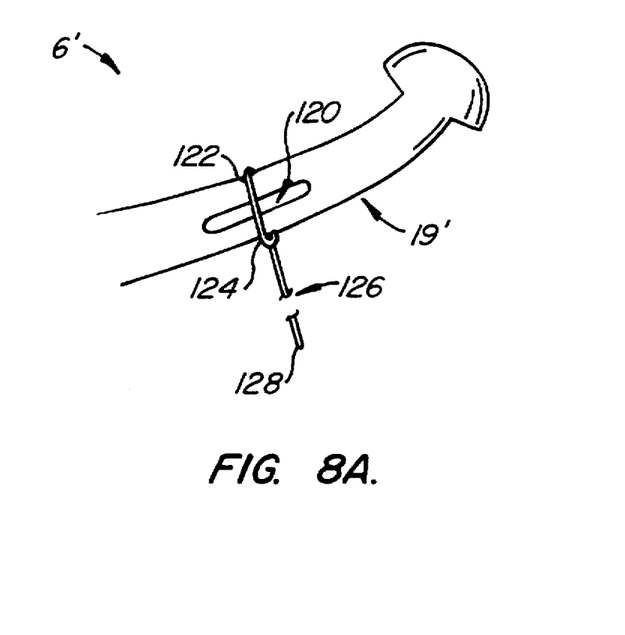
FIGS. 8A and 8B are side views of one of the anterior support members, illustrating an alternative embodiment in which the anterior support members can be folded to facilitate insertion into and removal from the patient's vagina.
Figure 8B:
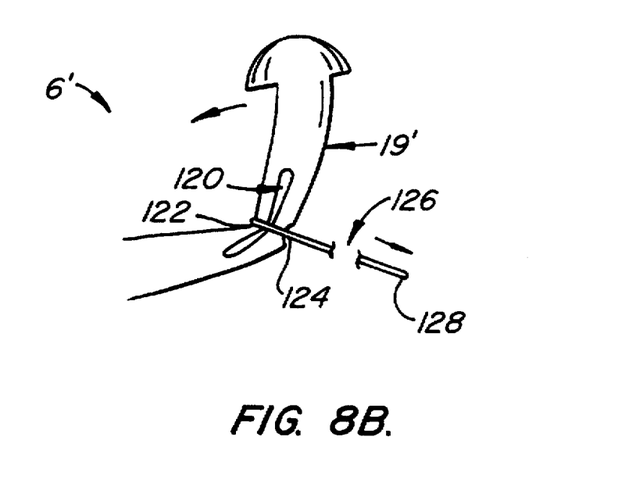

FIGS. 8A and 8B illustrate an alternative embodiment of an anterior support member 6', illustrating a method for folding support member 6 between an expanded, substantially elongate, configuration (FIG. 8A) for supporting the bladder neck and a collapsed configuration for insertion into and removal from the vagina (note that FIG. 8B only illustrates support member 6' in a partially collapsed configuration). As shown, arm 19' defines a slot 120 extending therethrough and a pair of notches 122, 124 one either side of slot 120. An elongate member, such as a string 126, is wrapped around arm 19' within notches 122, 124.

In use, the operator applies tension to string 126, which causes arm 19' to fold over slot 124 in the direction of the arrows in FIG. 8B. Folding arm 19' in this manner will facilitate the insertion and removal of the incontinence device into the patient's vagina. String 126 preferably has a length sufficient to extend toward the opening of the patient's vagina when the incontinent device is in position with anterior support member 6' engaged to the bladder neck. In this manner, the patient will be able to pull on a free end 128 of string 126 when removing the device.

Figure 9A:
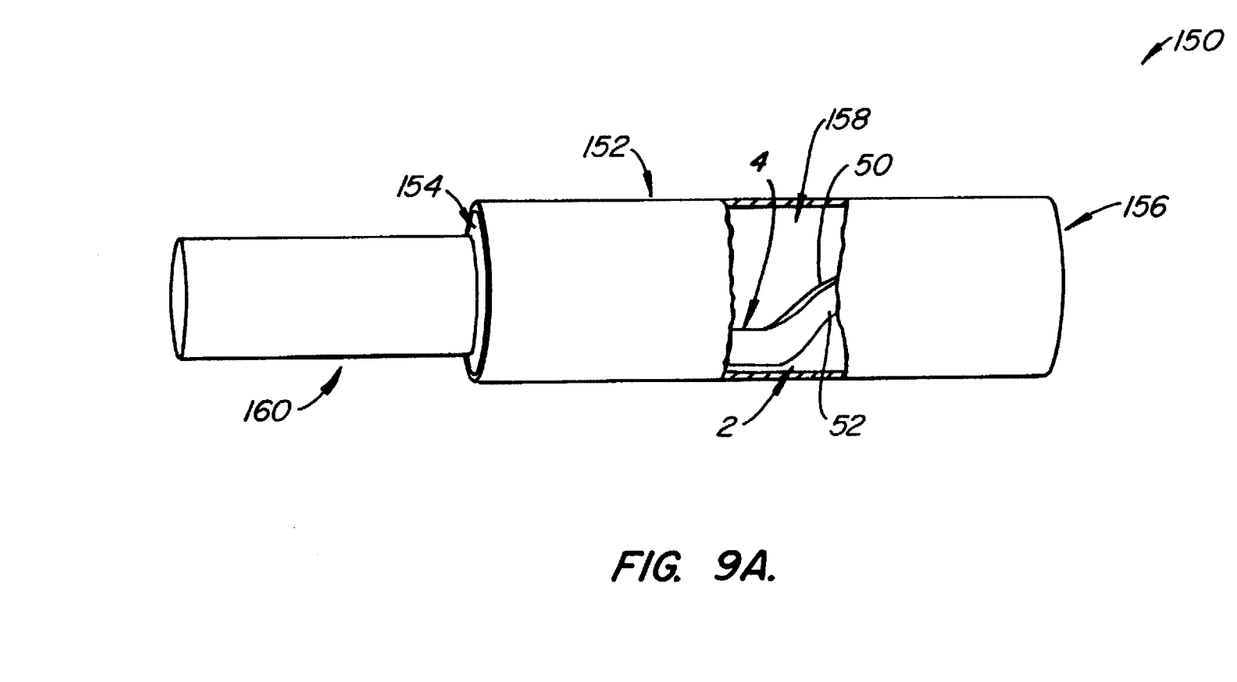
FIGS. 9A and 9B schematically illustrate an introducer and a method for inserting the incontinence device of FIG. 1 into the vagina.
Figure 9B:
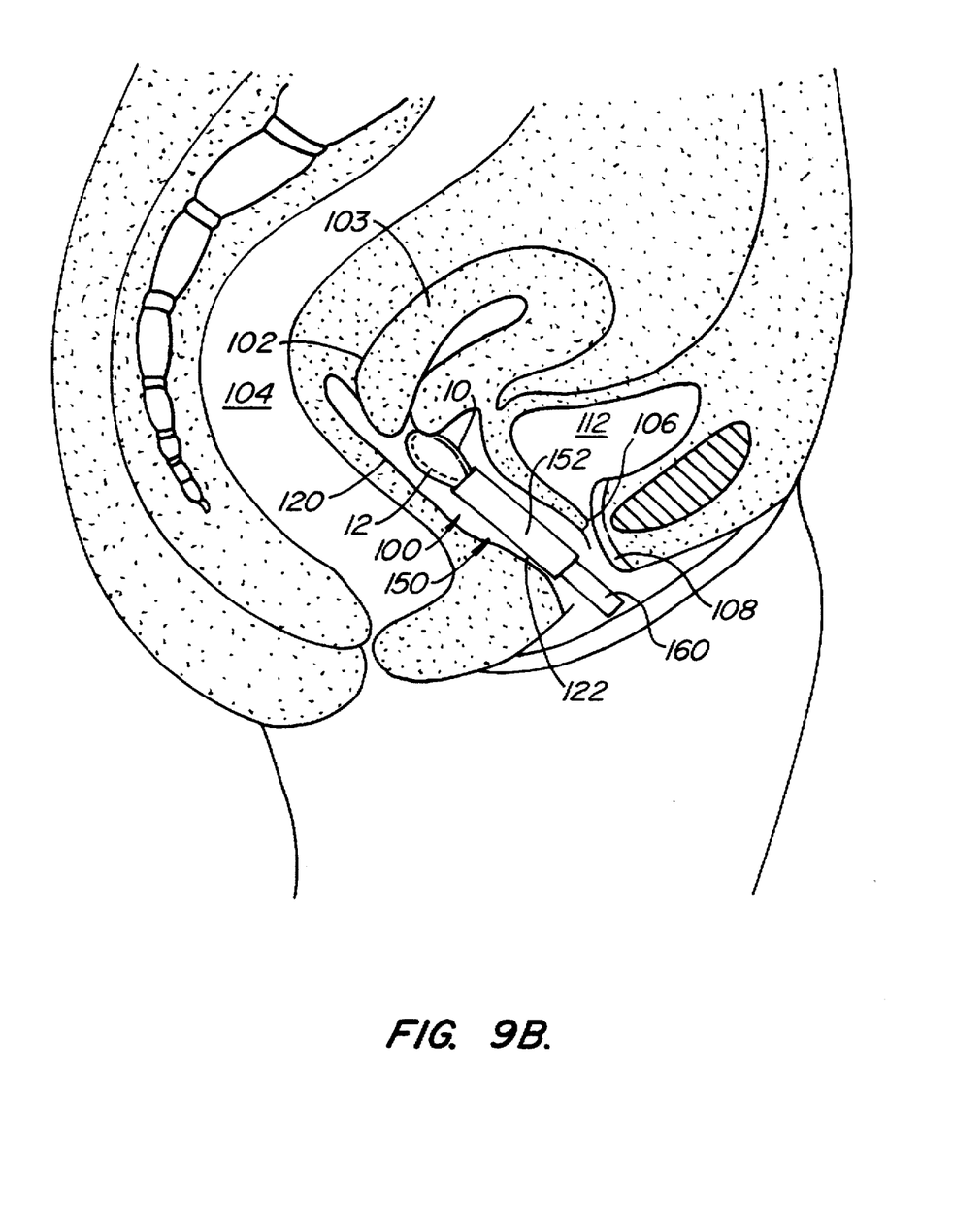

FIGS. 9A and 9b schematically illustrate an alternative system and method of inserting incontinence device 2 into the patient's vagina employing an introducer 150 instead of manually inserting device 2 as described above. Referring to FIG. 9A, introducer 150 comprises a hollow, cylindrical tube 152 having open proximal and distal ends 154, 156 and an axial lumen 158 therebetween sized to receive device 2 in the collapsed position. A pusher element, such as a piston 160 or the like, is used to propel device 2 from lumen 158.

As shown in FIG. 9A, for example, incontinence device 2 is collapsed and positioned within lumen 158 so that posterior support members 10, 12 face distal end 156 of tube 152. Tube 152 is then inserted into the patient's vagina 100 so that distal end 156 is positioned proximal of the posterior fornix 102 of the uterus 103 (see FIG. 9B). The patient or physician then moves piston 160 through proximal end 154 of tube 152 against device 2. Preferably, tube 152 is then withdrawn from the vagina while piston 160 holds device 2 in place. Device 2 automatically unfolds after tube 152 is withdrawn so that posterior support members 10, 12 bear against the pelvic structure and anterior support members 6, 8 are positioned on either side of the uretha 108 (see FIG. 5). In an alternative method, distal end 156 of tube 152 is positioned at the proximal end of the vagina and piston 160 is forced through tube 152 to propel incontinence device 2 through distal end 156.

Although the foregoing invention has been described in detail for purposes of clarity of understanding, it will be obvious that certain modifications may be practiced within the scope of the appended claims. For example, although the present invention has been described in terms of a disposable incontinence device, device 2 may comprise a more sturdy, biocompatible material, such as an elastomer, that remains continuously within the vagina for a period of one or more days or months. Alternatively, device may comprise a material that can be re-used. In this configuration, the patient may remove and cleanse the incontinence device when desired.

In addition, it should be clearly understood that the incontinence device of the present invention is not limited to a pair of anterior support members and a pair of posterior support members as described above and shown in the Figures. For example, device 2 may include a single posterior support member extending from end 16 of body 4. The posterior support member may simply be an extension of body, it may have a similar paddle shape as described above, or it may have a hemispherical shape, e.g., one that substantially conforms to the shape of the posterior vaginal wall. In addition, the device may comprise more than two anterior support members, if desired. Alternatively, the anterior support members may include a bridge or web portion that extends between the members to facilitate support of the bladder neck.

What is claimed is:

1. A method for treating female incontinence comprising:
   providing an elongate body having proximal and distal ends and a longitudinal axis therebetween and first and second anterior support members extending from the proximal end of the body;
   collapsing the first and second anterior support members into a substantially longitudinal configuration in close proximity with each other;
   inserting the anterior support members into the vagina of a patient;
   allowing the anterior support members to move into an expanded position spaced apart from each other; and
   positioning the first and second anterior support members on each side of the urethra to support the anterior vaginal tissue on either side of the bladder neck so that continence is preserved.

2. The method of claim 1 further comprising collapsing first and second posterior support members into a substantially longitudinal configuration in close proximity with each other and inserting the posterior support members into the vagina, wherein the posterior support members are attached to the anterior support members to brace the anterior support members against the bladder neck.

3. The method of claim 2 further comprising allowing the posterior support members to move apart from each other and positioning the posterior support members against the posterior vaginal wall on either side of the colon.

4. The method of claim 3 further comprising applying lateral pressure against the posterior vaginal wall with the posterior support members to brace the posterior and anterior support members and the elongate body member between the posterior vaginal wall and the urethra and provide longitudinal support to the anterior support members, thereby offering tissue tension to intra-bladder pressure so that continence is preserved.

5. The method of claim 2 wherein the anterior and posterior support members are folded towards each other into the longitudinal configuration.

6. The method of claim 5 further comprising axially folding the elongate body member into the longitudinal configuration.

7. The method of claim 2 further comprising biasing the anterior and posterior support members into the expanded position.

8. The method of claim 1 further comprising removing the elongate body and anterior support members from the vagina.

9. The method of claim 8 further comprising folding each anterior support member before the removing step.

* * * * *